(12) United States Patent  
Brauers et al.

(10) Patent No.: US 8,583,206 B2
(45) Date of Patent: Nov. 12, 2013

(54) SENSOR ARRANGEMENT AND METHOD FOR MONITORING PHYSIOLOGICAL PARAMETERS

(75) Inventors: Andreas Brauers, Aachen (DE); Alexander Douglas, Goirle (NL); Harald Reiter, Aachen (DE); Xavier Aubert, Brussels (BE)

(73) Assignee: Koninklijke Philips N.V., Eindhoven (NL)

( * ) Notice: Subject to any disclaimer, the term of this patent is extended or adjusted under 35 U.S.C. 154(b) by 277 days.

(21) Appl. No.: 12/597,339

(22) PCT Filed: Apr. 14, 2008

(86) PCT No.: PCT/IB2008/051409
§ 371 (c)(1),
(2), (4) Date: Oct. 23, 2009

(87) PCT Pub. No.: WO2008/129446
PCT Pub. Date: Oct. 30, 2008

(65) Prior Publication Data
US 2010/0113910 A1 May 6, 2010

(30) Foreign Application Priority Data
Apr. 24, 2007 (EP) .................................... 07106846

(51) Int. Cl.
*A61B 5/0408* (2006.01)
*A61B 5/0478* (2006.01)
*A61B 5/0492* (2006.01)
*A61B 5/0424* (2006.01)

(52) U.S. Cl.
USPC ........... 600/372; 600/382; 600/386; 600/388; 600/393

(58) Field of Classification Search
USPC .......................................... 600/372, 382–393
See application file for complete search history.

(56) References Cited

U.S. PATENT DOCUMENTS

| 4,763,660 A * | 8/1988 | Kroll et al. ..................... 600/391 |
| 5,578,359 A | 11/1996 | Forbes et al. |
| 5,968,854 A | 10/1999 | Akopian et al. |
| 6,870,109 B1 | 3/2005 | Villarreal |
| 7,412,281 B2 * | 8/2008 | Shen et al. ..................... 600/509 |
| 7,429,959 B2 * | 9/2008 | Gerder et al. ................. 343/718 |
| 7,559,902 B2 * | 7/2009 | Ting et al. ..................... 600/529 |
| 7,712,373 B2 * | 5/2010 | Nagle et al. ..................... 73/780 |
| 7,747,303 B2 * | 6/2010 | Eichler ........................ 600/390 |
| 2002/0019588 A1 | 2/2002 | Marro et al. |

(Continued)

FOREIGN PATENT DOCUMENTS

| EP | 1661512 A1 | 5/2006 |
| EP | 1731094 A1 | 12/2006 |
| WO | 0137286 A1 | 5/2001 |
| WO | 02068921 A2 | 9/2002 |

(Continued)

*Primary Examiner* — Lee S Cohen

(57) ABSTRACT

The invention refers to a sensor arrangement with at least one sensor and a method for monitoring physiological parameters of a person, a textile fabric and a use of a textile fabric. An sensor arrangement is described that is suited to improve signal quality and suppress noise, for instance in remote capacitive sensing of body parameters. To achieve this, certain textile fabrics are used, preferably integrated into textile used in a bed, e.g. the blanket, the bed cover, or the mattress. These textile fabrics allow for a suppression of electromagnetic interference from external sources and can be arranged to avoid charge build-up during measurements, in particular those caused by movements of the person.

16 Claims, 12 Drawing Sheets

(56) References Cited

U.S. PATENT DOCUMENTS

2006/0030767 A1* 2/2006 Lang et al. .................... 600/372
2006/0183989 A1* 8/2006 Healy ........................... 600/372
2008/0064964 A1* 3/2008 Nagata et al. ................. 600/484

FOREIGN PATENT DOCUMENTS

| WO | 2004045407 A1 | 6/2004 |
| WO | 2004100784 A2 | 11/2004 |
| WO | 2006131855 A2 | 12/2006 |

* cited by examiner

SENSOR ARRANGEMENT AND METHOD FOR MONITORING PHYSIOLOGICAL PARAMETERS

FIELD OF THE INVENTION

The invention refers to a sensor arrangement with at least one sensor and a method for monitoring physiological parameters of a person, a textile fabric and a use of a textile fabric.

BACKGROUND OF THE INVENTION

Bedside monitoring of physiological parameters is standard in hospital settings, for example for patients with cardiac diseases. It is also known to measure cardio data or pulmonary data at home. In WO 02/068921 A1, a bed equipped with force sensors and a central monitoring station has been described to monitor basically presence and activity of patients. Novel solutions to this task include mechanical and electrical and electromagnetic sensing of vital parameters using bed-integrated sensors. It is a drawback that these methods are prone to delivering false signals caused by electromagnetic interference (EMI) from the environment. This is especially true for inductive and capacitive measurements.

It is therefore an objective of the invention to provide a sensor arrangement and method for monitoring physiological parameters which is less susceptible to electromagnetic radiation.

The above objective is achieved by a sensor arrangement comprising at least one sensor for monitoring physiological parameters of a person and at least one textile fabric, the textile fabric comprising a conductive shielding for suppressing electromagnetic interference with the sensor.

It is an advantage of the sensor arrangement according to the invention that it allows to integrate an effective shielding into a bed, which reduces noise caused by electromagnetic interference, particularly during measurements using capacitive or inductive sensors or any other method sensitive to electromagnetic interference.

According to a preferred embodiment of the invention, the conductive shielding is connected to a potential equalization. The potential equalization may, in the sense of the embodiment, be an electric potential at which the conductive shielding is actively driven or a grounding. It is an advantage of the sensor arrangement according to this embodiment that static charges or dynamic charges which would disturb capacitive or inductive measurements, may be discharged via the textile fabric. The conductive shielding need not be a closed area, but is preferably composed of a net of conductive elements.

The textile fabric comprising the conductive shielding preferably does not otherwise interfere with daily routines of the person or, for example, hospital personnel. More preferably, it is not obviously visible and/or does not harm the design of a bed or bedroom. Most preferably, the textile fabric, which may be woven or non-woven, is conjoint with a suitable textile, i.e. a textile used in conjunction with a bed.

In a preferred embodiment, the textile fabric is at least part of a wearable garment, in particular of nightwear, like nightgown, pajama etc. According to another preferred embodiment, the textile fabric is integrated in a bed. More preferably, the textile fabric is part of a piece of bedclothes, for example a bed sheet, a pillow case or bed cover. Furthermore preferred, the textile fabric is part of a mattress, which is advantageously stationary, i.e. the mattress cannot be dislocated by the (sleeping) person.

In a further preferred embodiment of the invention, the sensor is integrated in the textile fabric. Advantageously, a plurality of functional elements may be integrated in the textile fabric. More preferably, the textile fabric comprises a layer structure of at least a shielding layer which comprises the conductive shielding, a sensing layer which comprises the sensor and an insulating layer, which is arranged between the shielding layer and the sensing layer. The relative proximity of the sensors to the shielding layer advantageously provides for effective shielding of the sensors.

According to still a further preferred embodiment of the invention, the sensor arrangement further comprises a contact for connecting the person to a potential equalization. Thus advantageously, the body of the person themselves is used as an additional shielding. Further the build up of electrostatic charge due to movements of the person is reduced. The contact is preferably a textile electrode which is, more preferably, arranged in a wearable garment, a bed sheet, a bed cover and/or a pillow.

According to still a further preferred embodiment of the invention, the sensor arrangement comprises two or more textile fabrics, each textile fabric comprising a part of the conductive shielding, wherein the parts of the conductive shielding are electrically connected. It is an advantage of this embodiment that the sensors may be shielded from more than one direction, the conductive shielding preferably surrounding the sensors, thus advantageously forming a kind of Faraday cage.

Preferably, one textile fabric is arranged in a bed cover and the other textile fabric is arranged in a bed sheet or mattress, thus advantageously shielding the sensors from electromagnetic radiation from top and bottom.

Another object of the present invention is a method of monitoring physiological parameters of a person, using at least one wearable or bed-integrated sensor, wherein the sensor is shielded from electromagnetic interference using a textile fabric comprising a conductive shielding. It is an advantage of the method according to the invention that the textile fabric comprising the conductive shielding does not otherwise interfere with daily routines of the person or, for example, the hospital personnel.

Another object of the present invention is a textile fabric with a layer structure comprising at least a sensing layer with at least one sensor, a shielding layer comprising a conductive shielding for suppressing electromagnetic interference with the sensor.

It is an advantage of the textile fabric according to the present invention that a plurality of functional elements is integrated therein. The relative proximity of the sensors to the shielding layer advantageously provides for effective shielding of the sensors. The textile fabric preferably further comprises an insulating layer, the insulating layer being arranged between the shielding layer and the sensing layer.

Another object of the present invention is a use of a textile fabric comprising a conductive shielding for suppressing electromagnetic interference with a bed-integrated or wearable sensor. The use of the textile fabric in connection with bed-integrated or wearable sensors advantageously provides electromagnetic shielding without an undue interference with the daily routines of a person the sensors are allocated to, or, for example, of the hospital personnel.

SUMMARY OF THE INVENTION

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference Figs. quoted below refer to the attached drawings.

DETAILED DESCRIPTION OF THE EMBODIMENTS

Figure 1A:
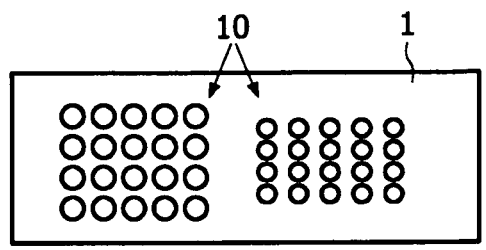
FIGS. 1a and 1b illustrate schematically an example of bed-integrated sensors.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Figure 1B:
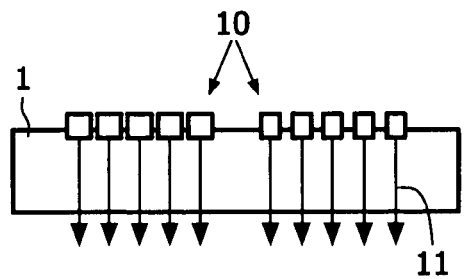
Figure 2A:
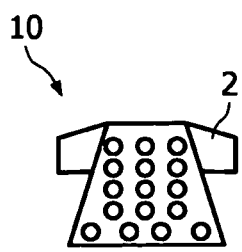
FIGS. 2a and 2b illustrate schematically examples body-wearable sensors.
Figure 2B:
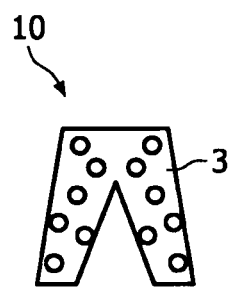

In FIGS. 1a, 1b, 2a and 2b illustrate schematically examples of bed-integrated sensors and body-wearable sensors. Sensors 10, like for example, capacitive or inductive or direct contact electrodes are shown which are integrated in bed clothing (FIGS. 1a and 1b) and in garment (FIGS. 2a and 2b). The sensors 10 may for example be integrated into a bed sheet 1 as depicted in FIG. 1a. FIG. 1b shows a schematic cross-section of the bed sheet 1 where leads 11 are visible which connect the sensors 10 to any suitable kind of analyzing electronics which is not depicted. FIG. 2a shows a shirt 2 with integrated sensors 10. FIG. 2b depicts trousers 3 fitted with sensors 10. Depending on the geometry of the sensors 10 different shielding options apply.

Figure 3A:
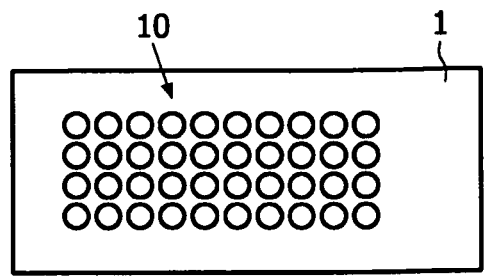
FIGS. 3a and 3b illustrate schematically an embodiment of the sensor arrangement and the textile fabric according to the invention.
Figure 3B:
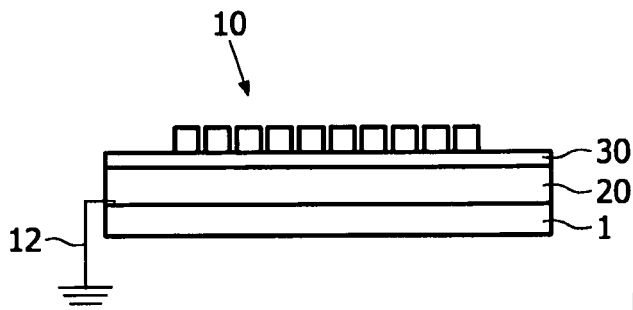

In FIGS. 3a and 3b, one possible approach is schematically depicted, wherein a conductive shielding 20 is integrated as a layer in a bed below a person (both not depicted) whose physiological parameters are measured by the sensors 10 in the bed sheet 1. The conductive shielding 20 can be, for example, a metal plate, a net of metal stripes or conductive yarns. The conductive shielding 20 may be provided as a single device, comprised in a textile fabric, which are placed in the bed or integrated in the mattress (not depicted) or in the bed sheet. According to another embodiment, the bed sheet 1 comprises a layer structure, including a conductive shielding layer 20, one or more insulating layers 30 and a sensing layer with the sensors 30. The conductive shielding 20 is preferably connected to a potential equalization 12, here a grounding 12. The conductive shielding 20 need not necessarily be a closed area but can also be arranged as a net of conductive elements, e.g. yarns. The conductive yarns may be arranged as grids or meander-like but can also make up for the complete surface.

The depicted sensor arrangement according to the invention offers a good shielding against electromagnetic interference from the bottom area. In order to have the same on top of the person, a similar layer structure may be integrated in a bed cover 4, as depicted in FIGS. 4a and 4b.

Figure 4A:
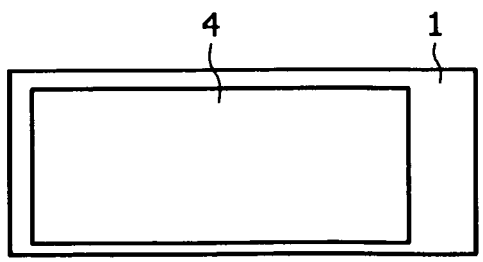
FIGS. 4a and 4b illustrate schematically another embodiment of the sensor arrangement according to the invention with the textile fabric according to the invention.
Figure 4B:
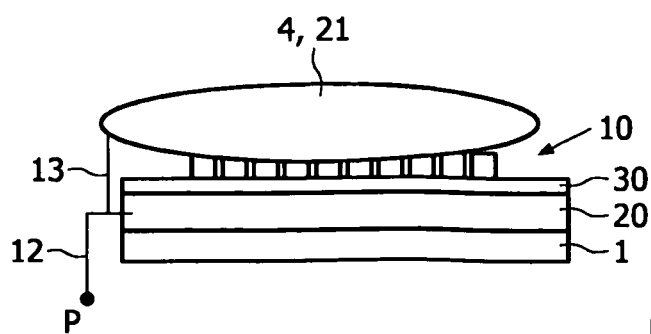

In FIG. 4a, a top view of the bed cover 4 covering the sensors 10 and partly the bed sheet 1 is depicted. Again, the person in the bed and the bed itself are not depicted. As is best seen in FIG. 4b, a part 21 of the conductive shielding 20 is integrated in the bed cover 4 and comprises an electrical connection 13 to the conductive shielding layer 20 in the bed sheet 1, the conductive shielding layer 20 again being connected to a potential equalization 12, here an electric potential P. The shielding layer 20 is thus actively driven at the electric potential. This way as well, charge build up on the person can be prevented, thus further preventing loss of sensitivity of the sensors 10 and preventing saturation of the measuring electronics. By the galvanic contact between the bed sheet 1 and the bed cover 4, the person and the sensors 10 are completely surrounded by a potential to take away any charge built up from movement during occupancy of the bed.

In another approach the body of the person themselves can be taken as a shielding. Here, it has to be warranted that the person is connected to a well-defined potential. This can be achieved by connecting the person either by textile electrodes in his nightwear or by using parts of the bed sheet or a pillow as a textile contact. In this case again, conductive textile fabrics can be used.

Referring now to FIGS. 5 through 14, measurement results are shown that give an indication of the effect of the textile fabric structure for shielding purposes. To show the effect of the textile fabric structure on the shielding capacity, nine different textile fabrics with conductive shielding were used to shield a capacitive sensor, used to measure electrocardiograms (ECGs) and electromyograms (EMGs) and electroencephalograms (EEGs) without galvanic contact to the skin. When placing such a sensor with the sensing electrode facing upwards, similarly to the sensor 10 integrated into the mattress or bed sheet 1 (FIGS. 1a, 1b), the sensor 10 detects signals present in the air. The shielding capability of a fabric can be observed by looking at the frequency spectrum of the signals detected by the sensor 10. Thus, in FIGS. 5 through 14, a sensor signal power in dBm (power measurement relative to 1 milliwatt) is given on the ordinate axes over a frequency in Hertz on the axes of abscissae. In FIGS. 6 through 12, two measurements are depicted per diagram. Generally, the dotted curve refers to a measurement with two coating layers of a textile fabric, whereas the full line refers to a measurement with a single layer of textile fabric.

EXAMPLES

Nine different textile fabrics, referred to in here as fabric 1 through fabric 9, have been used to shield the capacitive sensor. The fabrics can be divided into two categories:
Fabrics with metal based coatings.
Fabrics with polymer based coatings.

The fabrics coated with metal have a lower resistivity per square than the polymer coated fabrics. To prevent charge build up, it is beneficial to use a fabric with a low resistivity per square. Thus, the shield will have particularly the same potential all over, and therefore charge build up is prevented.

The frequency spectra of the different fabrics used for shielding are shown in FIGS. 6 through 14.

Figure 5:
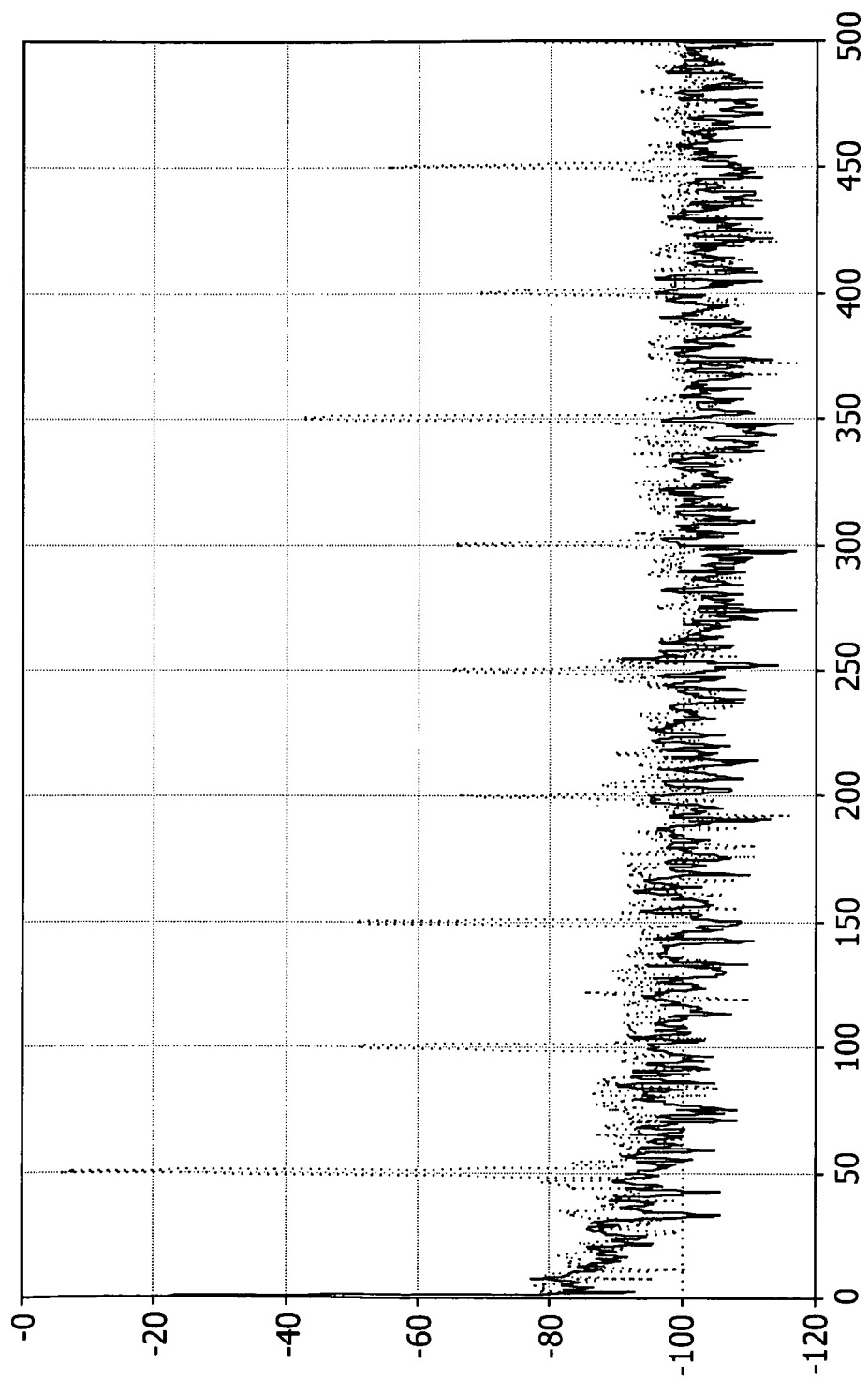
FIG. 5 illustrates an example of an unshielded capacitance sensor measurement versus a shielded capacitance sensor measurement in a diagram.

The spectrum in FIG. 5 shows the limits that can be obtained, by using the sensor without any shielding (dotted line), and when the shielding is realized by a closed metal box of 2.5 millimeter thick walls.

Figure 13:
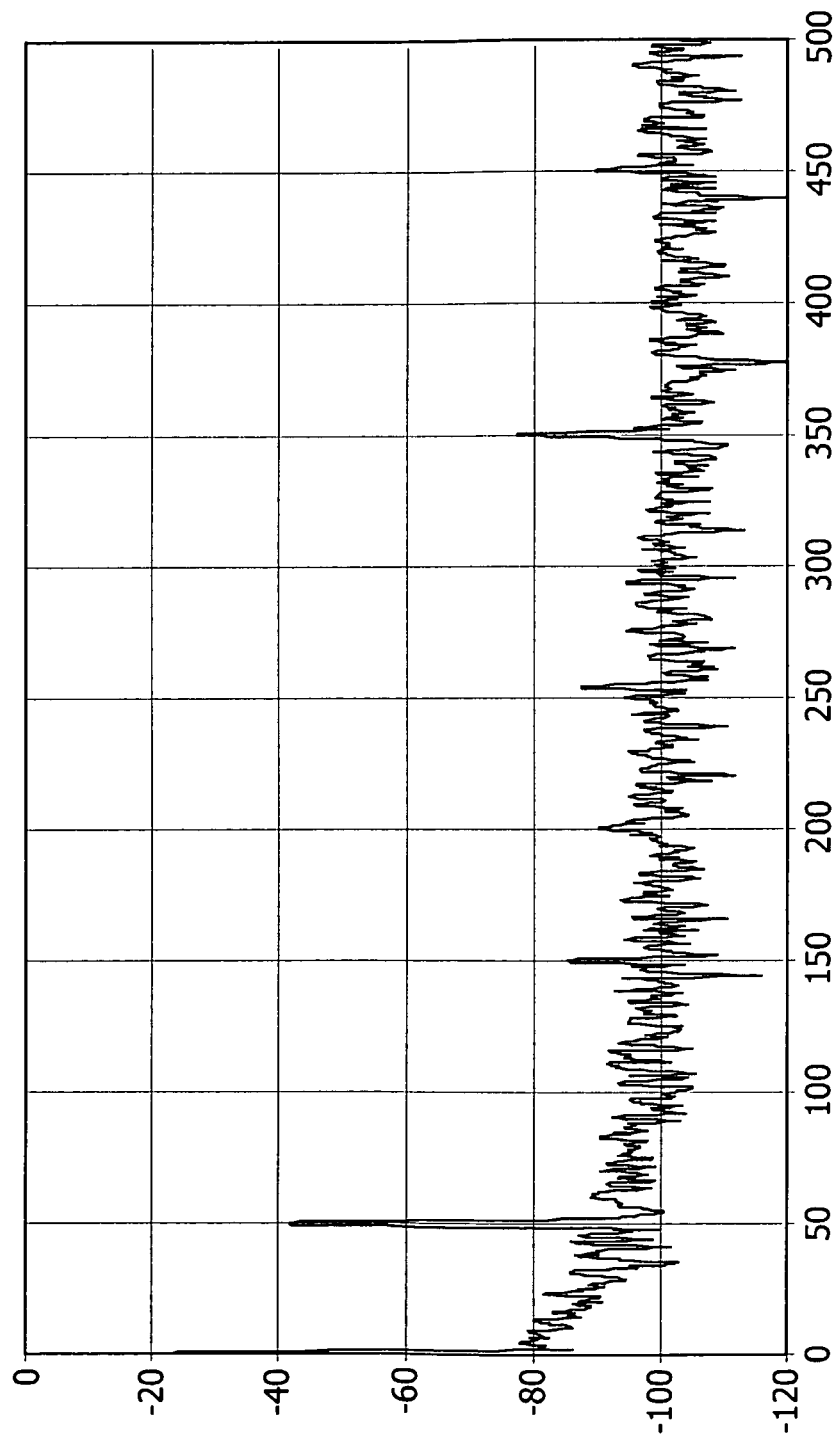
Figure 14:
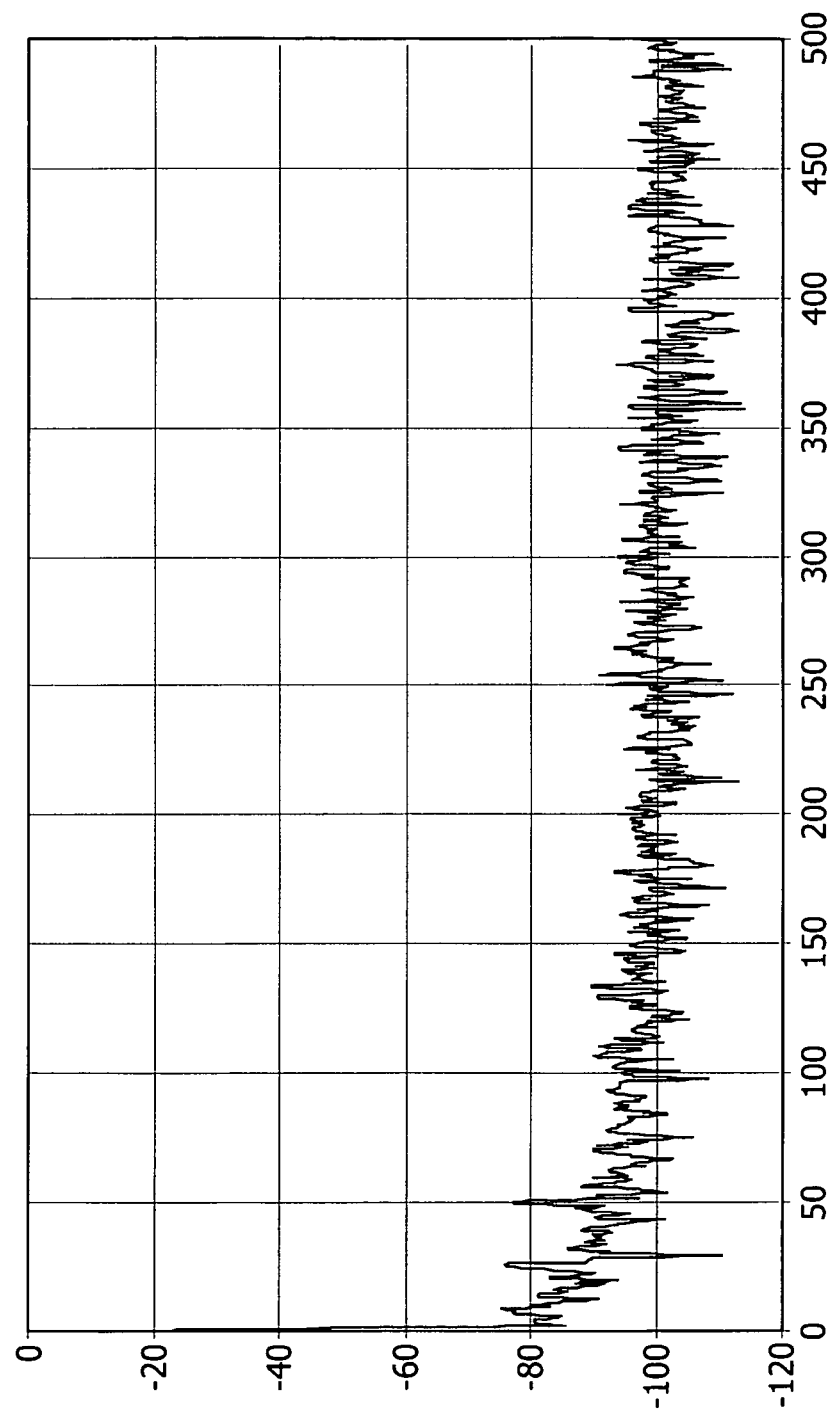

In FIGS. 13 and 14, the measurements of fabric 8 and fabric 9, both polymer coated fabrics, are shown. It can be concluded that the gaps in the fabric are relevant for its shielding capabilities. Fabric 8 is a mesh type fabric with holes in it, approximately 1.6 mm×1.8 mm wide. Fabric 9 on the other hand is a tightly woven fabric with considerably smaller gaps. Fabric 8 is not well suited to shield the sensor from 50 Hz, 150 Hz, 250 Hz, 350 Hz and 450 Hz.

Figure 9:
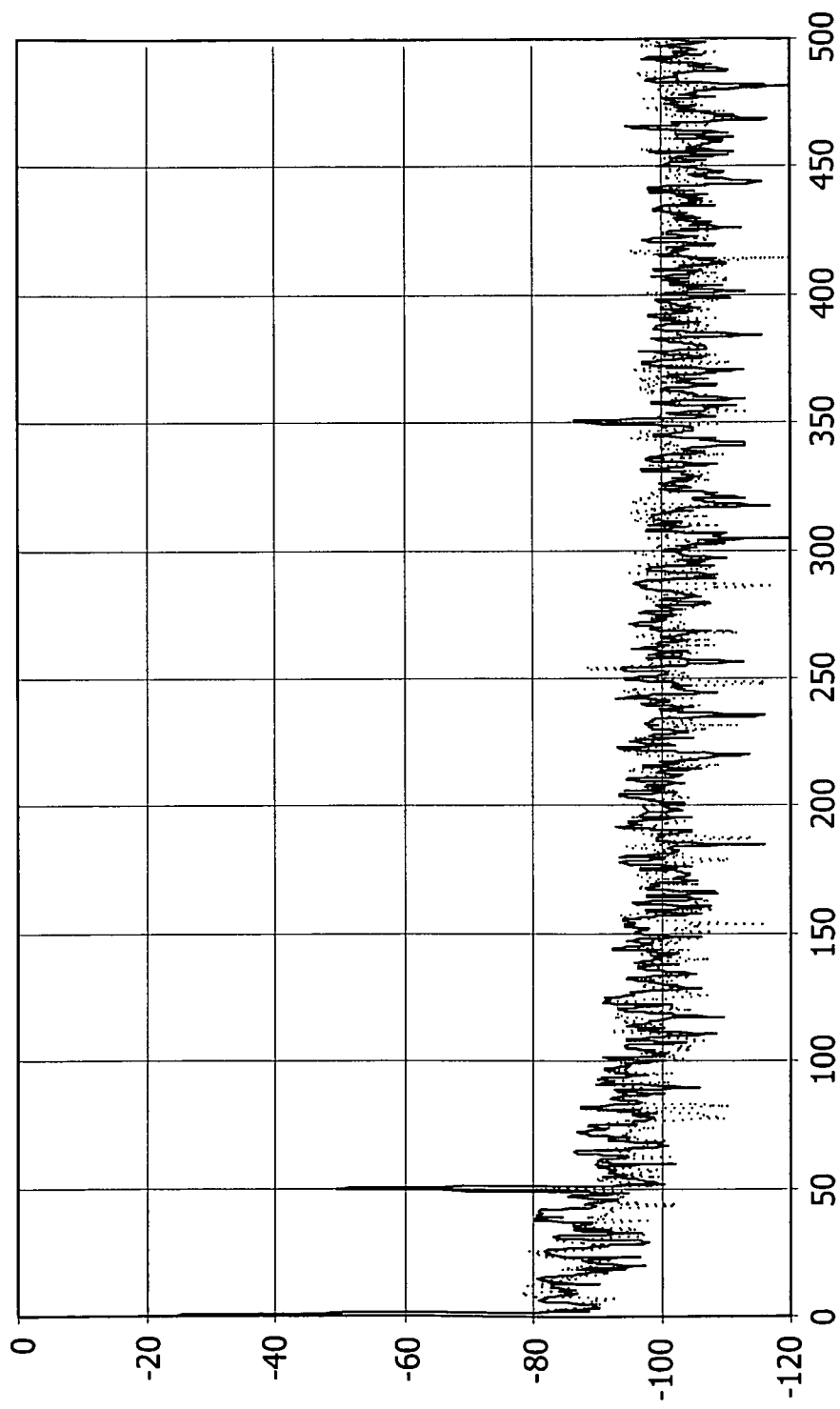

Referring to FIG. 9, the measurement of fabric 4 shows a comparable result. Fabric 4 is a fabric that has been knitted and is coated with a metal (silver). Fabric 4 also comprises a comparably open structure. From the measurements of fabric 4, it can be concluded that the size of the gaps in the fabric are relevant for the shielding capabilities. When a single layer of fabric 4 is used to shield the sensor (full line), the frequencies 50 Hz and 350 Hz are smaller than with an unshielded sensor (FIG. 5), but when using two layers of fabric 4, the influence of these frequency components on the sensor output is reduced further (dotted line). Using two layers, the gaps in the fabric are effectively reduced.

Figure 12:
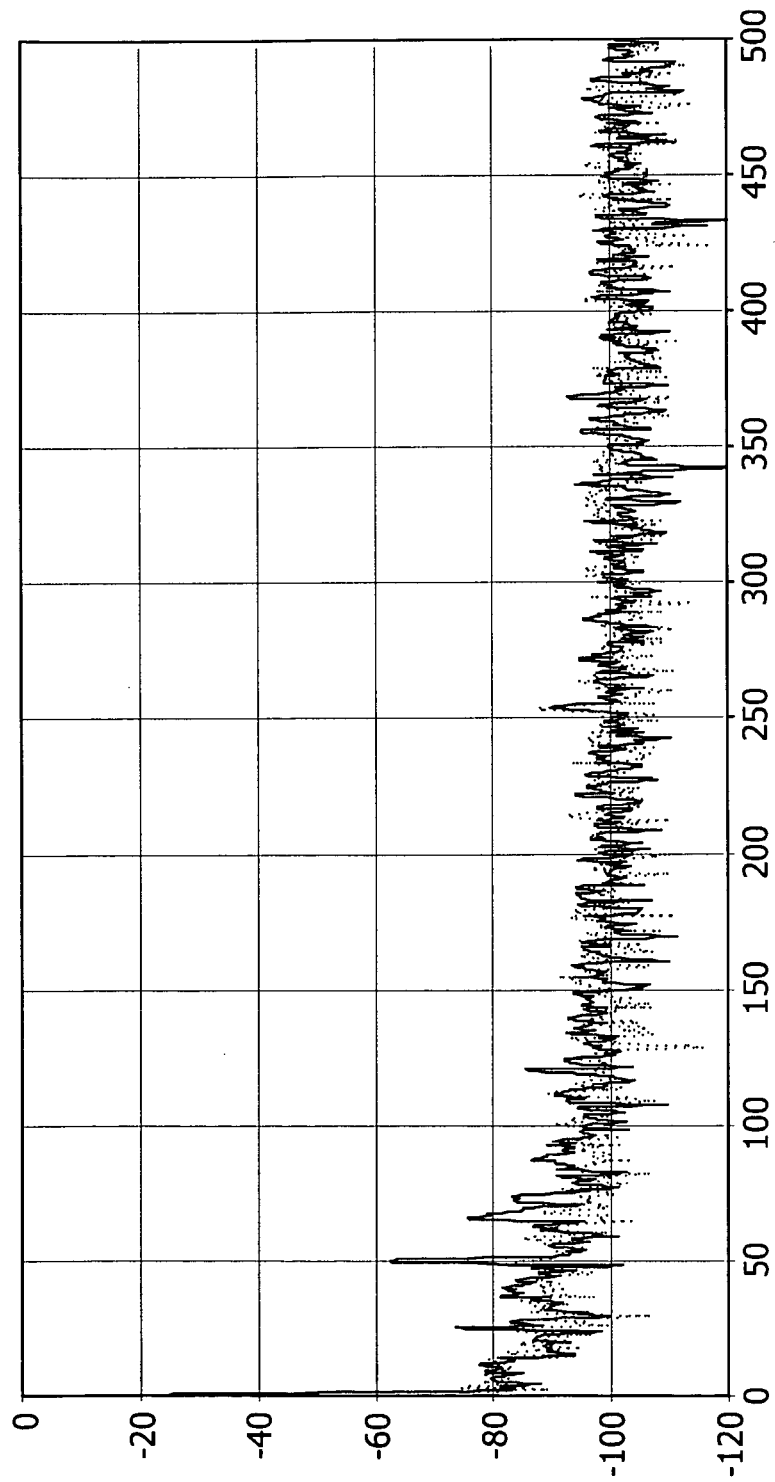

Referring now to FIG. 12, another fabric that has an open structure and that is coated with a metal (nickel over silver) is fabric 7. From the measurement of fabric 7 it can also be concluded that having two layers (full line) shields the sensor better than one layer (dotted line), and thus that a smaller gap size is better. Comparing the measurements of fabric 4 and fabric 7 it can be observed that two layers of fabric 7 shield the sensor better than two layers of fabric 4. With the naked eye, the gaps in fabric 4 and fabric 7 are equal in size. What is clearly visible is that fabric 7 (thickness 18 mils) is thicker than fabric 4 (8+/−1 mils).

Fabrics 1, 2, 3, 5, 6 and 9 are fabrics that do not have a clearly visible open structure like fabrics 4, 7 and 8. From the set of fabrics with a not clearly visible open structure, fabrics 2 and 6 are very similar in structure. Both are Nylon rip stop fabrics coated with a metal. Fabric 6 is coated with silver, and fabric 2 is coated with nickel over silver.

Figure 7:
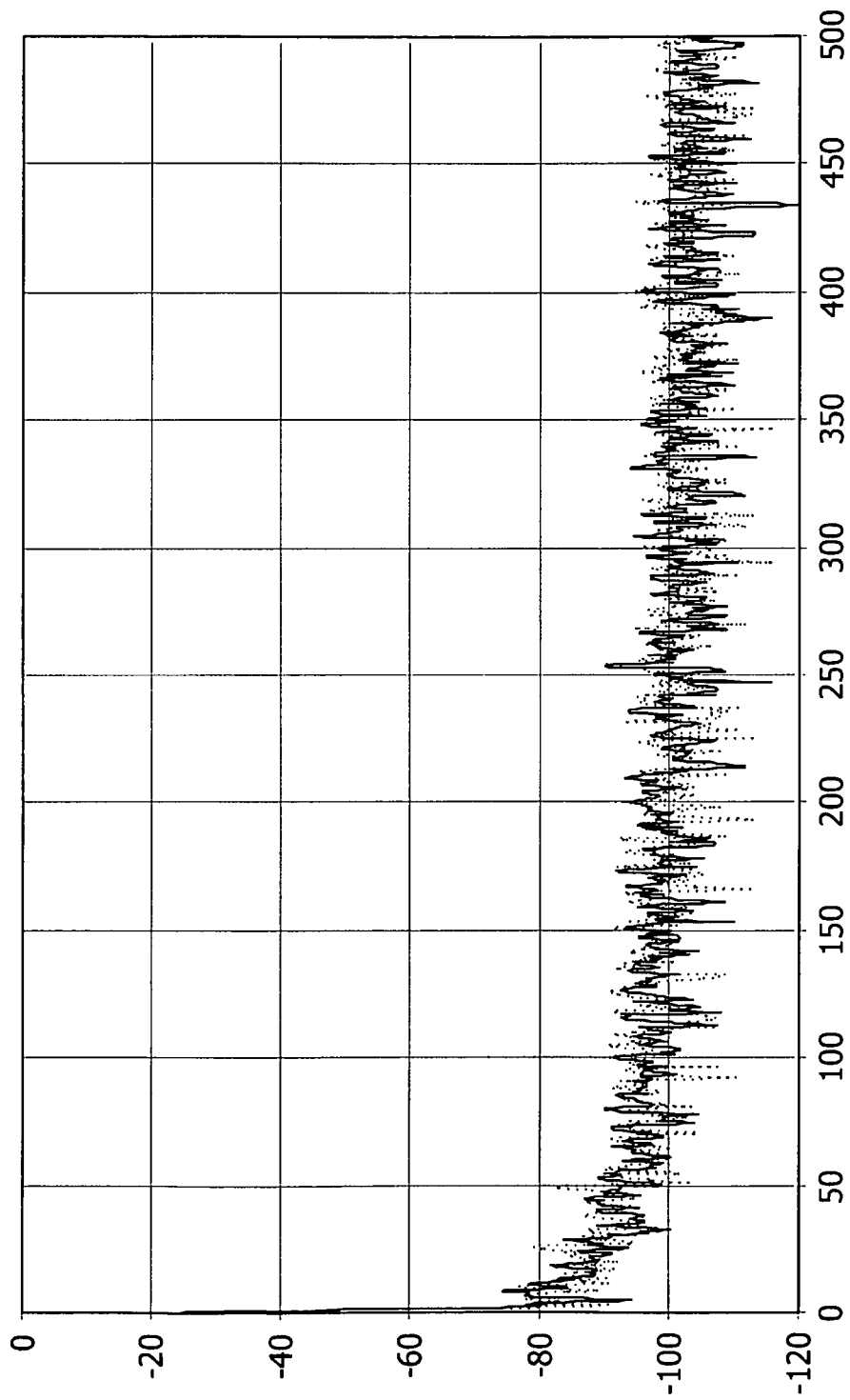
Figure 11:
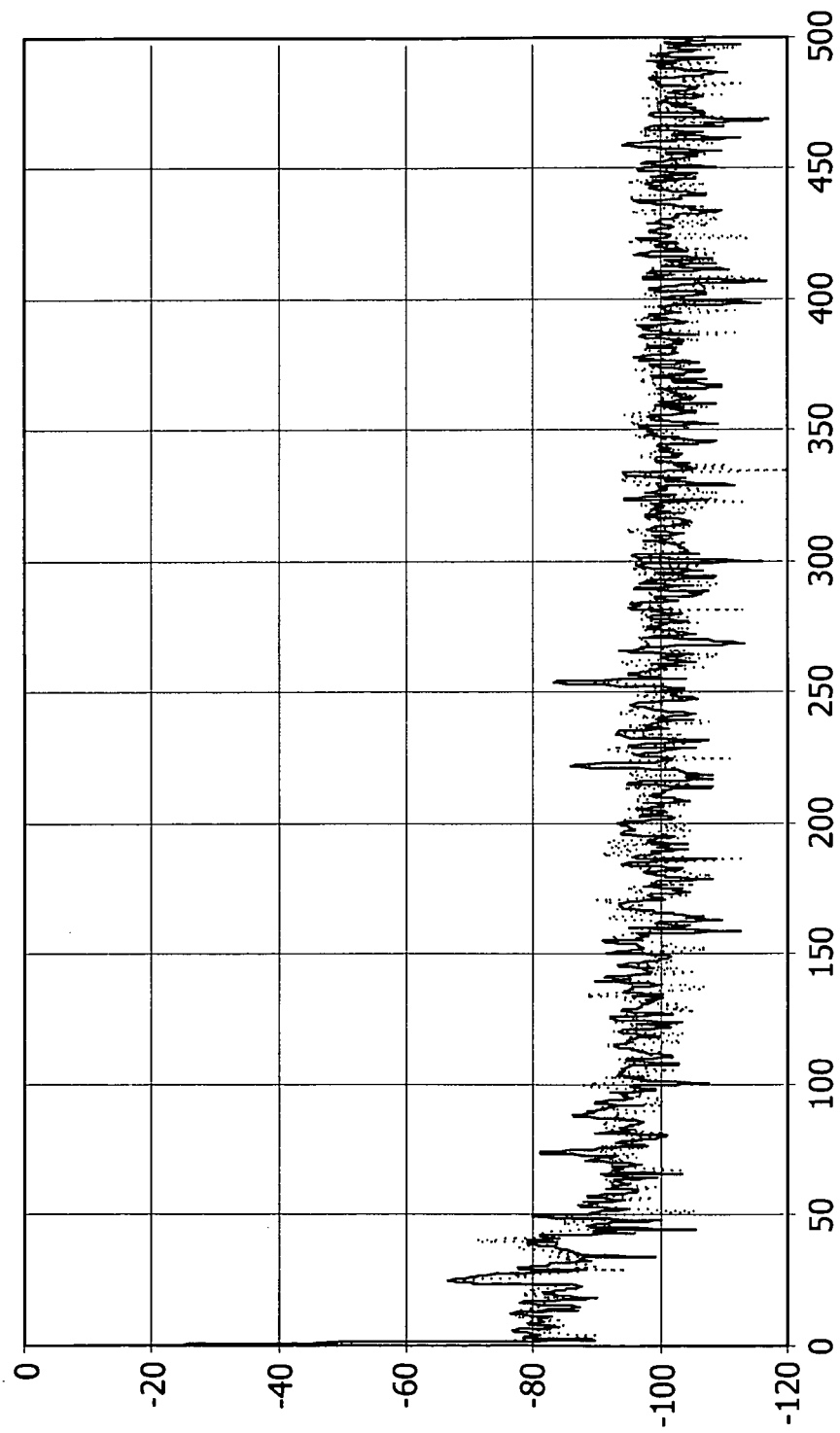

The measurements from fabric 2 and 6, depicted in FIGS. 7 and 11, clearly show different shielding behavior. Fabric 6 (FIG. 11) is not as good as fabric 2 (FIG. 7) in shielding the sensor from frequencies like 25 Hz, 50 Hz, 225 Hz and 250 Hz. Apart from this, the sensor output has a higher noise level in the frequency band from DC to about 250 Hz, which is relevant for measuring ECGs. Since the fabrics have the same structure but are different with respect to the surface resistivity, it is assumed that the shielding is also dependent on the surface resistivity. The surface resistivity of fabric 6 is less than 0.25 Ohm per square, and fabric 2 has a surface resistivity of less than 0.1 Ohm per square.

Figure 8:
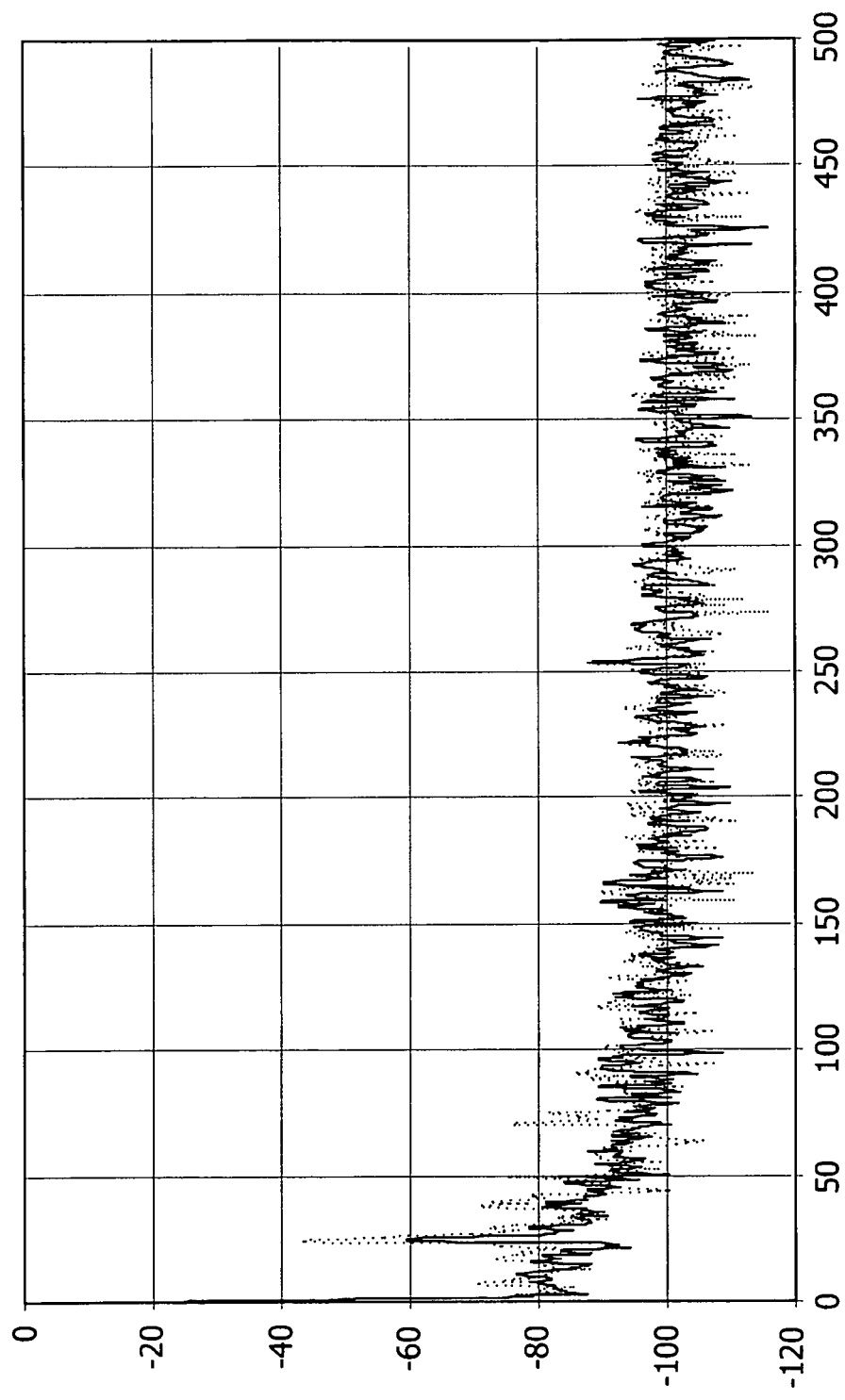
Figure 10:
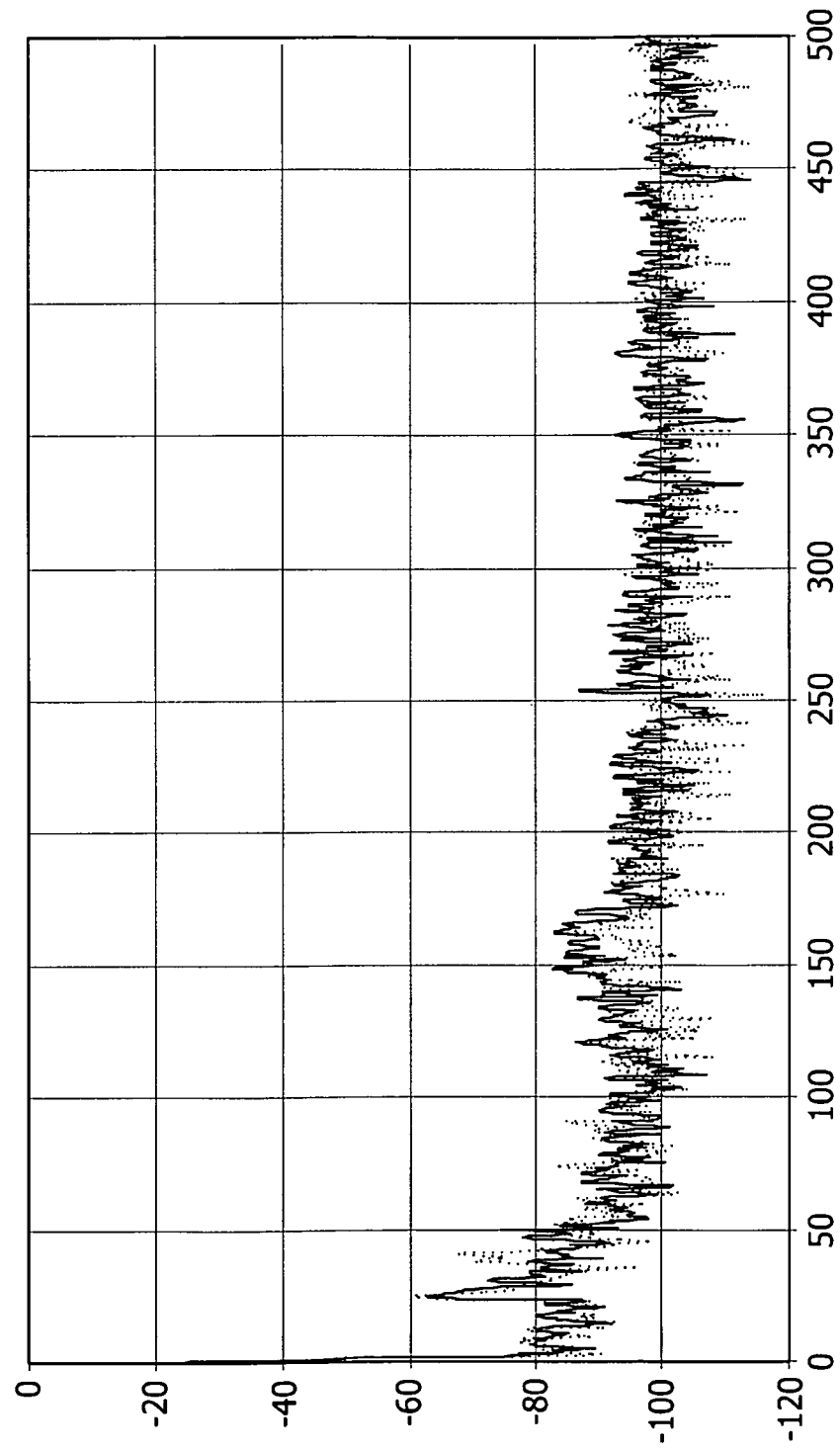

Referring now to FIGS. 8 and 10, fabric 3 and fabric 5 are both fabrics based on nylon threads, coated with silver. Both are also non-woven fabrics. Fabric 3 (FIG. 8) is a knitted fabric, and fabric 5 (FIG. 10) is a looped fabric. Even though the fabrics 3 and 5 appear to be thick, the measurements show that the shielding provided by fabrics 3 and 5 are not very good. Both these fabrics do not shield the sensor very well in the frequency range below 250 Hz. The noise level in this region is higher than with the other visible non-open structured fabrics tested.

Figure 6:
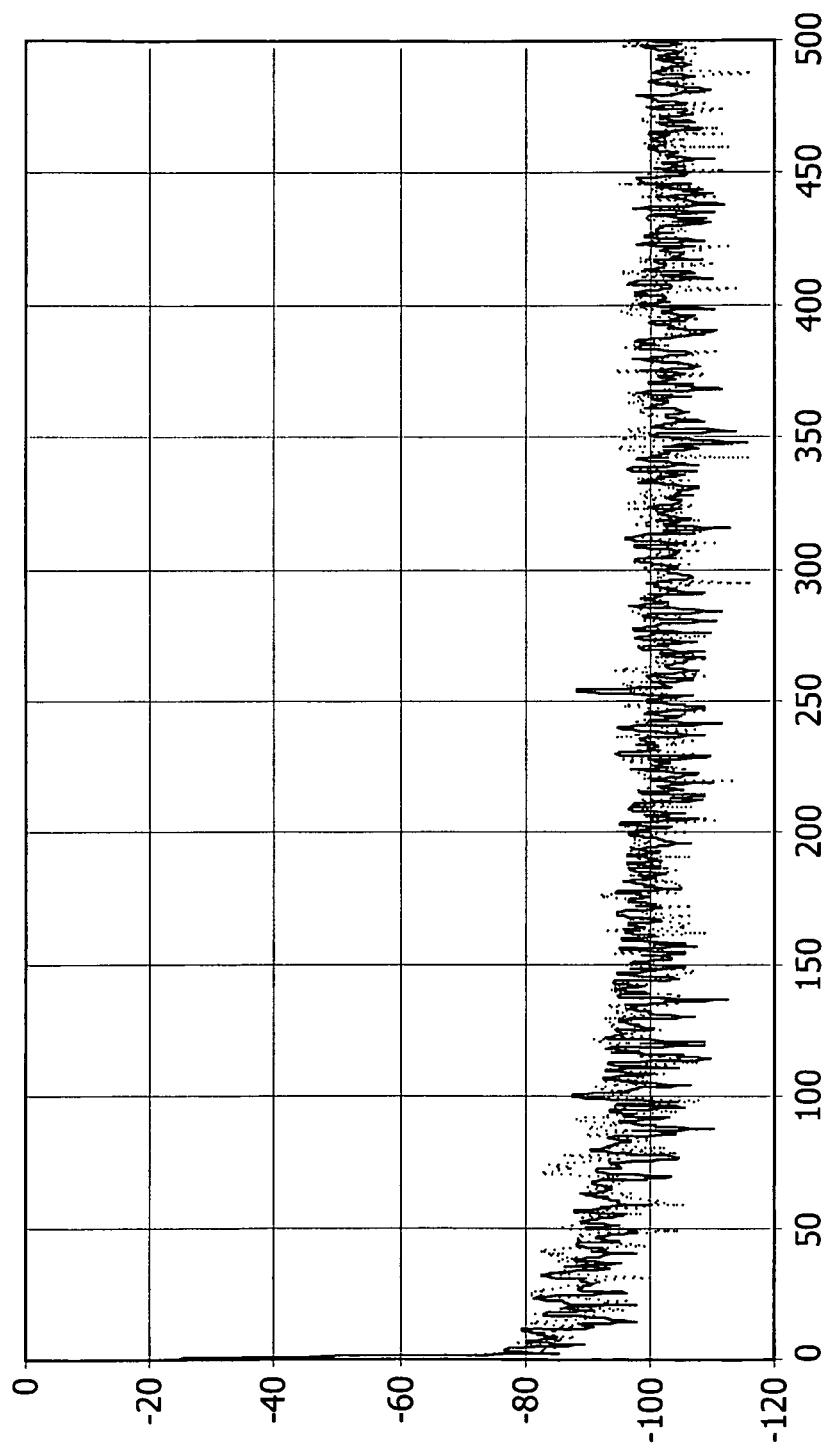
FIGS. 6 through 14 show measurements of a capacitance sensor shielded by different examples of textile fabrics according to the present invention.

The last fabric measured is fabric 1, the measurement depicted in FIG. 6. Fabric 1 is a so-called point-bonded fabric based on a nylon thread, coated with nickel over silver. Using only one layer of fabric 1 will not completely shield the sensor from the 250 Hz frequency (full line). Using two layers provides increased shielding for the 250 Hz (dotted line). Note that for an ECG measurement only frequencies up to 150 Hz are needed. For EMG the frequencies up to 500 Hz are relevant.

The invention claimed is:

1. Sensor arrangement comprising at least one sensor for monitoring physiological parameters of a person and at least two textile fabrics, each of the textile fabrics comprising a part of a conductive shielding, wherein the parts of the conductive shielding are electrically connected, the conductive shielding of the textile fabrics surrounding the at least one sensor and having at least one of a metal based coating or a polymer based coating for suppressing electromagnetic interference with the sensor.

2. Sensor arrangement according to claim 1, wherein the conductive shielding is connected to a potential equalization.

3. Sensor arrangement according to claim 2, further comprising a contact for connecting the person to the potential equalization.

4. Sensor arrangement according to claim 1, wherein one of the textile fabrics is integrated in a bed.

5. Sensor arrangement according to claim 4, wherein the one of the textile fabrics is part of a mattress.

6. Sensor arrangement according to claim 1, wherein the sensor is integrated in one of the textile fabrics.

7. Sensor arrangement according to claim 1, wherein one of the textile fabrics comprises a layer structure of at least a shielding layer comprising the conductive shielding, a sensing layer comprising the sensor and an insulating layer, the insulating layer being arranged between the shielding layer and the sensing layer.

8. Sensor arrangement according to claim 1, wherein one textile fabric is arranged in a bed cover and the other textile fabric is arranged in a bed sheet or mattress.

9. A method, comprising:
monitoring physiological parameters of a person using at least one wearable or bed-integrated sensor;
shielding the sensor from electromagnetic interference,
wherein the sensor is shielded from electromagnetic interference using two or more textile fabrics surrounding the at least one wearable or bed-integrated sensor, each of the textile fabrics comprising a conductive shielding having at least one of a metal based coating or a polymer based coating.

10. Textile fabric with a layer structure comprising at least a sensing layer with at least one sensor, and a shielding layer comprising a conductive shielding having at least one of a metal based coating or a polymer based coating for suppressing electromagnetic interference with the sensor, wherein the shielding layer of two or more textile fabrics surrounds the at least one sensor.

11. Textile fabric according to claim 10, further comprising an insulating layer, the insulating layer being arranged between the shielding layer and the sensing layer.

12. Sensor arrangement comprising at least one sensor for monitoring physiological parameters of a person and two or more textile fabrics, each of the textile fabrics comprising a conductive shielding, the conductive shielding of the textile fabrics surrounding the at least one sensor and having at least one of a metal based coating or a polymer based coating for suppressing electromagnetic interference with the sensor.

13. Sensor arrangement according to claim 12, wherein the conductive shielding is connected to a potential equalization.

14. Sensor arrangement according to claim 13, further comprising a contact for connecting the person to the potential equalization.

15. Sensor arrangement according to claim 12, wherein the sensor is integrated in the textile fabrics.

16. Sensor arrangement according to claim 12, wherein at least one of the textile fabrics comprises a layer structure of at least a shielding layer comprising the conductive shielding, a sensing layer comprising the sensor and an insulating layer, the insulating layer being arranged between the shielding layer and the sensing layer.

* * * * *